United States Patent
Swanson, Sr.

(10) Patent No.: US 6,905,519 B2
(45) Date of Patent: Jun. 14, 2005

(54) METHOD OF FORMING TRANSFEMORAL SOCKETS AND LOCK ADAPTER THEREFOR

(75) Inventor: Verner M. Swanson, Sr., Temperance, MI (US)

(73) Assignee: Bionix Prosthetic Solutions, Inc., Toledo, OH (US)

(*) Notice: Subject to any disclaimer, the term of this patent is extended or adjusted under 35 U.S.C. 154(b) by 91 days.

(21) Appl. No.: 10/173,498

(22) Filed: Jun. 17, 2002

(65) Prior Publication Data

US 2002/0193887 A1 Dec. 19, 2002

Related U.S. Application Data

(60) Provisional application No. 60/298,541, filed on Jun. 15, 2001.

(51) Int. Cl.[7] .................................................. A61F 2/80
(52) U.S. Cl. ........................................................ 623/36
(58) Field of Search ............................... 623/33–37, 27; 403/65, 68, 52, 119, 181, 232.1; 292/300–301

(56) References Cited

U.S. PATENT DOCUMENTS

| 2,698,196 | A | * | 12/1954 | Mangus .................... 292/300 |
| 5,529,576 | A | * | 6/1996 | Lundt et al. ................. 623/38 |
| 6,051,026 | A | * | 4/2000 | Biedermann et al. ......... 623/38 |
| 6,440,173 | B1 | * | 8/2002 | Meyer ......................... 623/36 |
| 2003/0074085 | A1 | | 4/2003 | Slemker et al. |

OTHER PUBLICATIONS

Prosthetic Design, Inc., Clayton, Ohio, FLEXCON advertisement, at least as early as Mar. of 2002.

* cited by examiner

Primary Examiner—Alvin Stewart
(74) Attorney, Agent, or Firm—Marshall & Melhorn, LLC

(57) ABSTRACT

A lock adapter is adapted to connect a residual limb liner with locking pin to a transfemoral prosthetic limb. The lock adapter is formed of a bracket having a first end and a second end, and preferably has a generally S-shaped configuration. The first end of the bracket has a first mounting face against which the lock is to be secured. The second end of the bracket is provided with a second mounting face against which the prosthetic limb is to be secured. The bracket being is formed so that the first and second mounting faces are spaced apart from one another, and may optionally be angled relative to one another. Methods of forming transfemoral test and final sockets are provided.

12 Claims, 12 Drawing Sheets

METHOD OF FORMING TRANSFEMORAL SOCKETS AND LOCK ADAPTER THEREFOR

RELATED APPLICATION

This application is claiming the benefit, under 35 U.S.C. § 119(e), of the provisional application filed Jun. 15, 2001 under 35 U.S.C. § 111(b), which was granted Ser. No. 60/298,541. This provisional application is hereby incorporated by reference.

BACKGROUND OF THE INVENTION

The invention relates to prosthetic devices and methods of forming the same. In particular, the invention relates to a method of forming both transfemoral test and finished thermosetting or laminated sockets, and a lock adapter for connecting a residual limb transfemoral socket to a lock mechanism and prosthetic knee joint.

A transfemoral prosthetic limb is conventionally secured to an amputee's residual limb stump by securing the prosthetic limb to a rigid socket assembly. This may commonly be done by through the use of a locking pin. In this technique, the amputee first dons a sock-like liner formed of an elastomer and may include fabric cover. The lower or distal end of the liner is formed of a rigid material, such as urethane, and the locking pin extends from this rigid bottom. These liners are well known in the art. The pin is extended through the wall of the socket and a distal adapter mounted within or outside of the socket, and can be locked onto a prosthetic lock mounted to the prosthetic limb to secure the prosthesis.

Typically, the pin has a longitudinal series of rack-like serrations and extends through a pin bore of the lock body. The teeth of a pinion gear in the lock body extend into the pin bore to engage the teeth of the lock pin therein. The pinion gear is mounted for one way rotation to permit entry of the lock pin into the pin bore but lock the lock pin against removal. The lock pin can be released only by moving the pinion gear in a direction parallel to its rotational axis until it disengages from the lock pin, e.g., via a manual release button.

In accordance with the conventional transfemoral sockets and attachment locking assemblies, a connecting mechanism is employed in which the lock in the socket is mounted in line with the prosthetic knee. In some amputees, especially those with mid to longer length above knee amputations, this creates a gate disturbance as the knee center is dropped below the knee center of the sound limb. The conventional connecting mechanisms are further incapable of incorporating any flexion in the locking mechanism, which might beneficially accommodate the hip flexion contractures that are often associated with above knee amputations.

Thus, it would advantageous to provide an improved transfemoral socket and lock adapter which allowed for a length off-set between the lock and the prosthetic knee, and which further allowed for the desired degree of flexion, if any. It would further be advantageous to provide improved methods of forming test and finished transfemoral sockets using such lock adapters.

SUMMARY OF THE INVENTION

The invention is directed to a lock adapter for connecting a residual limb liner provided with a locking pin at its lower end that is releasably engaged with a lock affixed to a transfemoral prosthetic limb. The lock adapter is formed of a bracket having a first end and a second end, and preferably has a generally S-shaped configuration. The first end of the bracket has a first mounting face against which the lock is to be secured. This first mounting face thus defines a first longitudinal axis that is perpendicular to the mounting face. The second end of the bracket is provided with a second mounting face against which the prosthetic limb is to be secured. The second mounting face defines a second longitudinal axis perpendicular thereto, and the bracket being is formed so that the first and second longitudinal axes are spaced apart from one another.

In addition, the bracket may optionally be formed so that the first longitudinal axis is angled relative to the second longitudinal axis. This configuration allows for the placement of a variety of degrees of flexion, preferably in a range greater than 0 degrees and less than or equal to 25 degrees.

The bracket may preferably be configured so that, in use, the first end of the bracket is forward of and below the second end of the bracket. This provides a length off-set between the lock and the prosthetic knee so that the prosthetic knee center may be raised to the level of the knee center of the sound limb.

Any known lock adapted for use with the desired liner locking pin maybe secured to the first mounting face of the bracket. The lock may be secured to the first mounting face by any suitable means, such as by the use of threaded fasteners, welding, adhesives or the like. In one preferred embodiment, the lock is formed integrally with the first end of the bracket.

In another aspect, a method is provided for forming a transfemoral test socket incorporating a lock in such a manner that the lock is removable and reusable. The method comprises providing a lock adapter assembly comprising a bracket having a first end and a second end and a lock secured at the first end of the bracket, the lock being adapted to releasably engage a locking pin of a residual limb liner. A lower portion of the lock is masked with a masking material and the lock adapter assembly is fastened to a model of a portion of a residual limb. A polymeric transfemoral socket is then molded about the lock adapter assembly. Subsequently, the masking material is removed and the model is separated from the socket. The masking material is preferably in the form of a fabrication block.

Further, a one-step method is provided for forming a transfemoral final socket, comprising providing a lock adapter assembly comprising a bracket having a first end and a second end and a lock secured at the first end of the bracket, the lock being adapted to releasably engage a locking pin of a residual limb liner. The lock adapter assembly is secured to a model of a portion of a residual limb, and one or more fibrous reinforcing layers are positioned about the model and lock adapter assembly. A flowable polymeric resin is applied to the one or more reinforcing layers to form a transfemoral socket about the model and lock adapter assembly. The model is later separated from the socket.

DETAILED DESCRIPTION OF THE PREFERRED EMBODIMENTS

Figure 1:
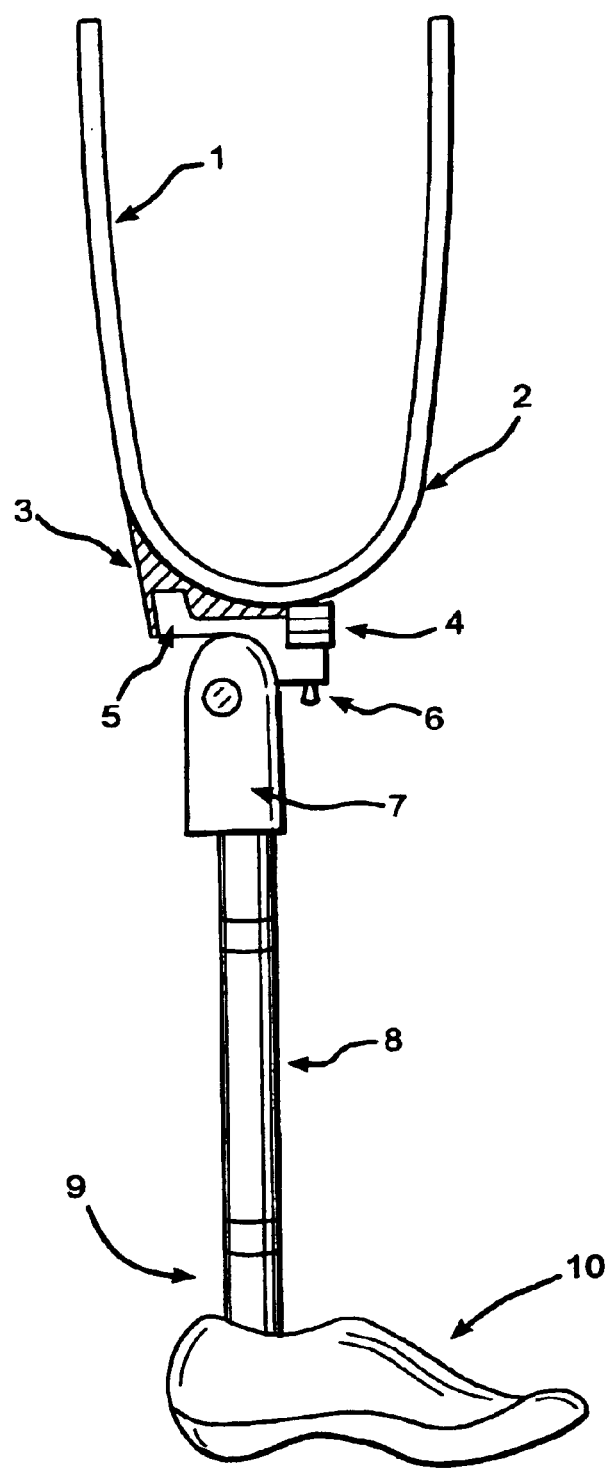
FIG. 1 is a somewhat schematic side elevational view, partially in section, of a thermoformed thermoplastic test socket connected to an artificial leg with a lock adapter in accordance with the invention.

Referring now to the drawings, FIG. 1 illustrates a lock adapter 5 of the present invention is used to connect and fabricate a residual limb transfemoral socket 2 to a lock mechanism 4 and a knee joint 7. The lock adapter 5 is preferably of a generally S-shaped configuration, as shown. In the illustrated embodiment of FIG. 1, the prosthesis includes a pylon 8 secured to the knee joint 7, the pylon 8 being in turn connected to an artificial foot 10 by means of the ankle assembly 9.

Figure 2:
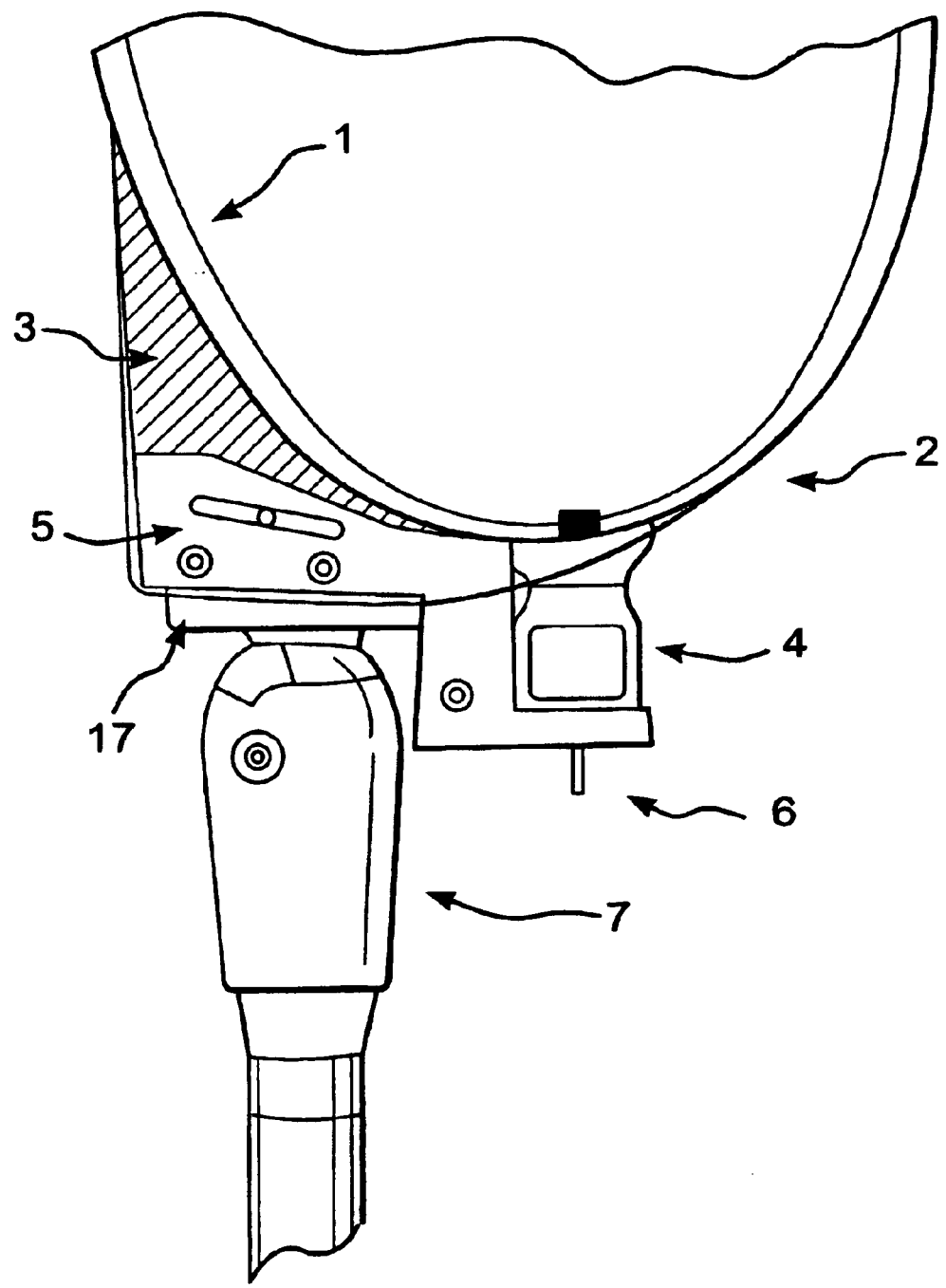
FIG. 2 is an enlarged view, partially in section, of the device shown in FIG. 1.

In the embodiment shown in FIG. 2, the transfemoral socket 2 has a posterior foam filler 3 to provide the shape of the distal posterior inner aspect of the socket 2. The knee joint 7 is connected to the lock adapter 5 by means of suitable fasteners, such as four threaded holes 15, best illustrated in the exploded view of the lock adapter 5 in FIG. 4, with fastener screws. The lock adapter can be connected to the knee joint 7 directly, or by means of an adapter, such as the pyramid adapter 17. As illustrated, the conventional suction liner 1 is provided with a locking pin 6 that may be releasably engaged by the lock or locking mechanism 4.

Figure 3:
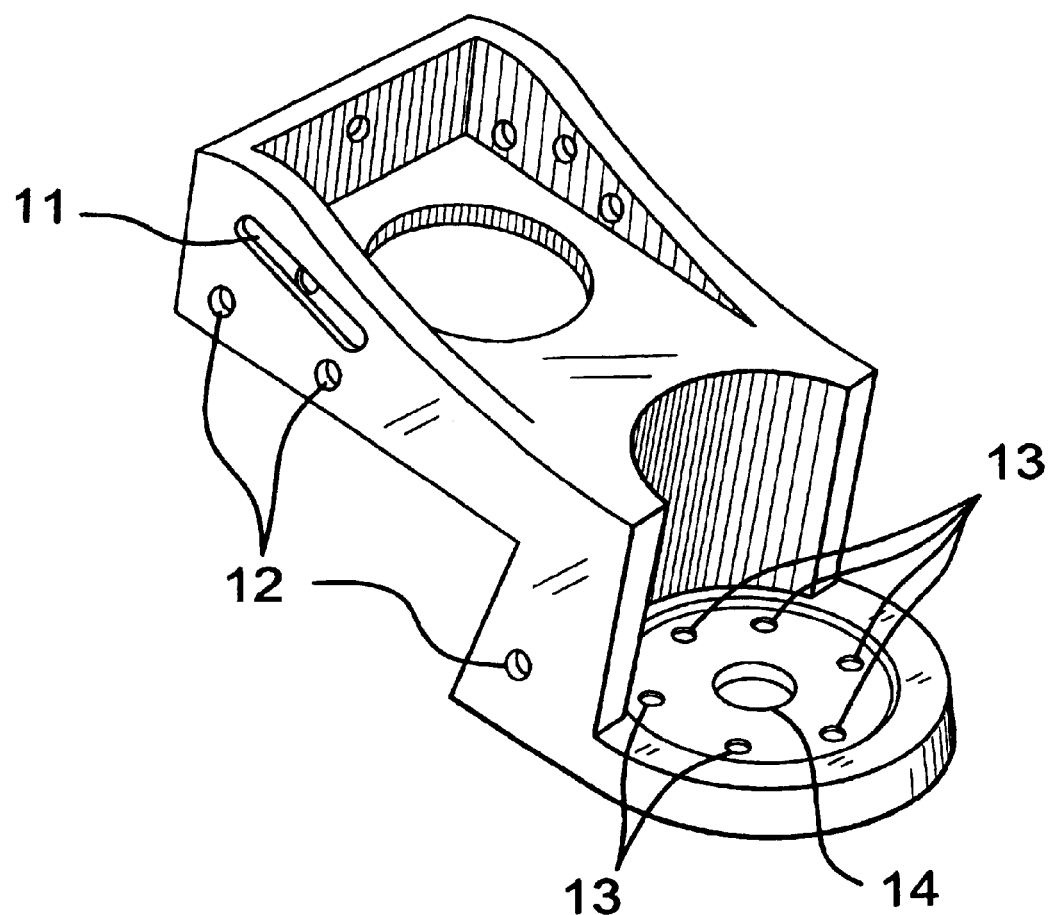
FIG. 3 is a perspective of the lock adapter illustrated in FIG. 2.

FIG. 3 is a perspective of the lock adapter of the invention. As shown in FIG. 3, the lock adapter 5 has threaded holes 12 which are used to fasten the lock adapter 5 to the transfemoral thermoplastic socket 2 (FIG. 1) with, for example, machine screws 34. The cutout notched cavities 11 are preferably included to provide for additional anchoring to the thermoplastic socket 2 (FIG. 1). The drilled through holes 13 are provided to connect the lock mechanism 4 to the lock adapter 5 with fastener screws 36 (FIG. 4).

Figure 4:
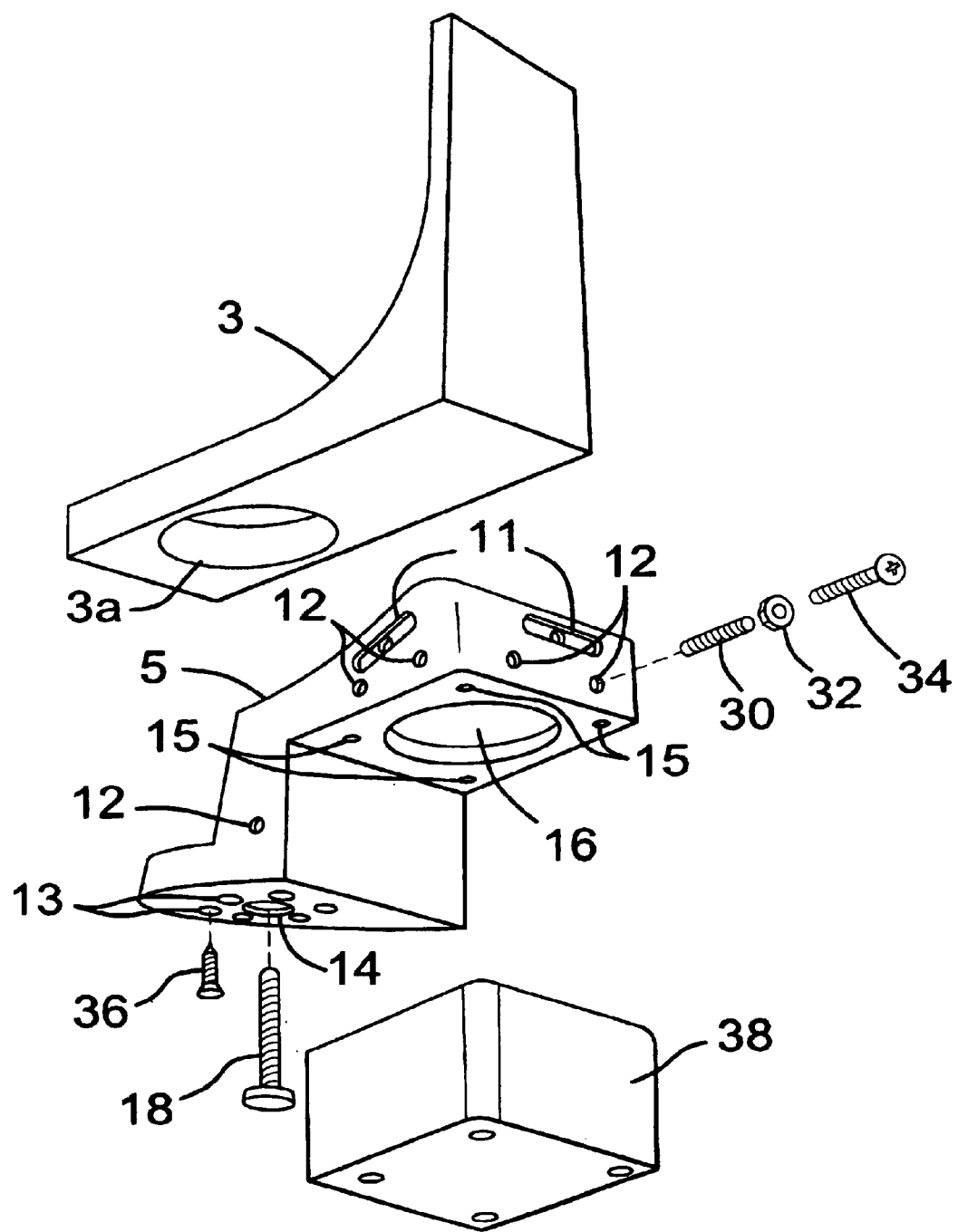
FIG. 4 is an exploded perspective view of the lock adapter shown in FIG. 2, the posterior foam filler and the fabrication block.

As further shown in FIG. 4 the posterior foam filler 3 has a cut out hole 3a sized and shaped to allow the passage of the lock mechanism 4 (FIG. 2). The fabrication block 38 is fastened to the lock adapter 5 via screw holes 15 with the socket head cap screws 40. The set screws 30 are provided to mark the location of the threaded screw holes 12 in the thermoplastic. The set screws 30 are removed after the thermoplastic socket 2 (FIG. 1) is fabricated. The set screws 30 are then replaced with washers 32 and socket head cap screws 34 to fasten the lock adapter 5 to the thermoplastic socket 2 (FIG. 1).

A preferred method for fabricating the transfemoral test socket in accordance with the present invention is as follows. A negative cast is made of the residual limb and suction liner 1 (FIG. 1) with front and side alignment lines. This negative cast is filled with molding plaster and the fill pipe is set parallel to the alignment lines. After the mold has set the negative cast material is removed and the result is a positive cast (not shown).

The positive cast will be used as a model for the transfemoral socket 2 (FIG. 1). The positive cast is modified by adding or removing material to achieve proper weight bearing in the transfemoral socket. The modifications are done to the positive cast in accordance with standard principals of prosthetics. The positive cast may also be made by using computer aided design and a computer lathe to manufacture the positive mold. The positive mold is painted with a mold sealer to reduce moisture.

A nylon is applied to the mold to provide a vacuum channel. The lock mechanism is fastened to the lock adapter with fastener screws 36 through the attachment holes 13, as shown in FIG. 4. The fabrication block 38 is attached to the lock adapter 5 at the four threaded holes 15 with the socket head cap screws 40.

The posterior foam filler 3 is placed around the lock mechanism 4 and inside the support walls on the lock adapter 5, as shown in FIG. 2. The set screws 30 (FIG. 4) are installed in the threaded holes 12 to mark the location in the thermoplastic socket. These set screws 30 are left protruding out of the lock adapter 5 an appropriate amount to mark the location of the holes 12.

The lock adapter 5 and lock mechanism 4 are attached to the positive mold with a fastener screw 18 through the center hole 14 in the lock adapter 5 and lock mechanism 4. The center hole 14 is preferably tapped so that various suction adapters and/or cosmetic adapters (not shown) may be threadedly attached thereto. Examples of suitable suction adapters would include a plug to completely seal the center hole, a plug incorporating a one-way valve, and a lock pin cover.

The lock adapter 5 is positioned on the positive mold so that the lock mechanism 4 is horizontal to the fill pipe representing the negative cast alignment lines. The lock adapter 5 is positioned on the positive mold so that the knee joint 7 will have the amount of knee rotation as determined by the Prosthetist.

The thermoplastic sheet, cut to the appropriate size, is placed and heated in a wide oven at the appropriate forming temperature. The positive mold is placed horizontally in a vacuum fixture for thermoforming the plastic under negative pressure. The thermoplastic is removed from the oven when the plastic is ready and moldable. The thermoplastic sheet is applied to the positive mold. A seam is formed along the lower aspect of the positive mold. The thermoplastic is pinched along the seam and held until the vacuum pulls in the plastic into all the undercuts so that there are no air voids.

After the thermoplastic cools, the plastic is sanded down on top of the lock mechanism fastener screw 18. The fastener screw 18 is then removed. The fabrication block 38 is trimmed out, for example with a cast cutter and sanding router, and the four attachment screws 40 are removed along with the fabrication block 38.

The thermoplastic socket is removed from the positive mold using compressed air or the mold is broken out of the socket with, for example, a pneumatic chisel. The thermoplastic socket material is sanded down to the top of the set screws 30 using a sanding router. The set screws 30 are removed with a hex wrench, and the fastener screws 34 with washers 32 are installed and tightened in place of the set screws 30.

The edges of the thermoplastic socket material are sanded smooth. The transfemoral prosthesis is assembled with a knee joint 7, pylon 8, ankle assembly 9 and artificial foot 10, as illustrated in FIG. 1.

Figure 5:
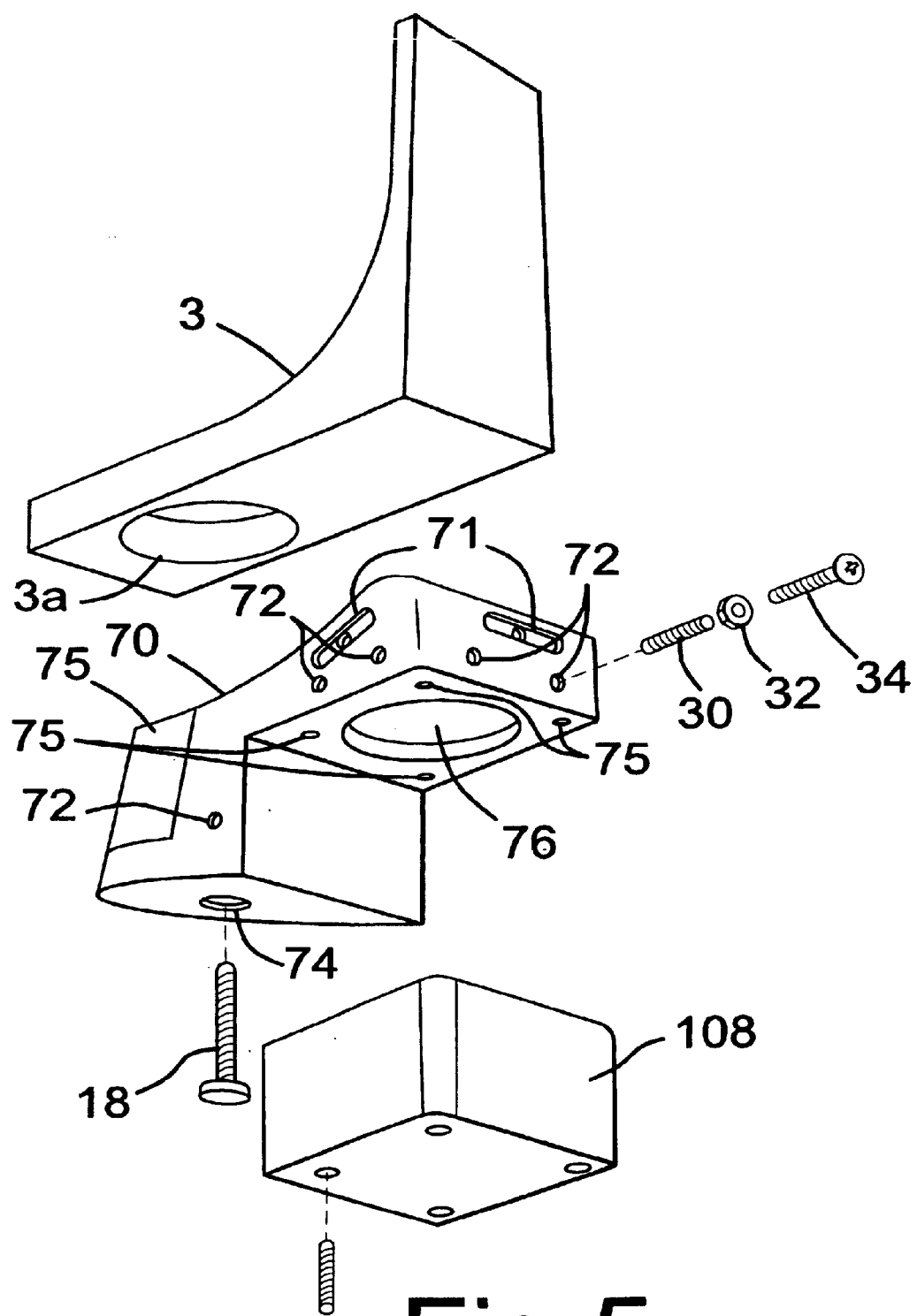
FIG. 5 is a perspective view of an alternate embodiment of the lock adapter of the invention.

As shown in FIG. 5, the lock adapter 70 is provided with integral locking mechanism 44 used to connect and fabricate the residual limb transfemoral socket 2 (FIG. 1) to the knee joint 7. In this embodiment, at least a portion of the housing for the locking mechanism is formed integrally with the lock adapter 70. The remainder of the lock adapter is the same as in the first embodiment. Thus, as shown in FIG. 5 the lock adapter 70 has threaded holes 72 which are used to fasten the lock adapter 70 to the transfemoral thermoplastic socket 2 (FIG. 1) with machine screws 34. The cutout notched cavities 71 provide additional anchoring to the thermoplastic socket 2 (FIG. 1).

As further shown in FIG. 5, the posterior foam filler 3 has a cut out hole 3a to go around the lock mechanism 44. The fabrication block 38 is fastened to the lock adapter 70 via screw holes 75 with the socket head cap screws 40. The set screws 30 are again provided to mark the location of the threaded screw holes 72 in the thermoplastic. The set screws 30 are removed after the thermoplastic socket is fabricated. The set screws 30 are replaced with washers 32 and socket head cap screws 34 to fasten the lock adapter 70 to the thermoplastic socket 2 (FIG. 1).

A preferred method for fabricating the transfemoral socket with lock adapter with integral locking mechanism is as follows. A negative cast is made of the residual limb and suction liner 1 (FIG. 1) with front and side alignment lines. This negative cast is filled with molding plaster and the fill pipe is set parallel to the alignment lines. After the mold has set the negative cast material is removed and the result is a positive cast (not shown).

The positive cast will be used as a model for the transfemoral socket. The positive cast is modified by adding or removing material to achieve proper weight bearing in the transfemoral socket. The modifications are done to the positive cast in accordance with standard principals of prosthetics. The positive cast may also be made by using computer aided design and a computer lathe to manufacture the positive mold.

The positive mold is painted with a mold sealer to reduce moisture. A nylon is applied to the mold to provide a vacuum channel. The fabrication block 38 is attached to the lock adapter 70 at the four threaded holes 75 with the socket head cap screws 40. The posterior foam filler 3 is placed around the locking mechanism 44 and inside the support walls on the lock adapter 70.

The set screws 30 are installed in the threaded holes 72 to mark the location in the thermoplastic socket. These set screws are left protruding out of the lock adapter an appropriate amount to mark the location.

The lock adapter 70 with integral locking mechanism 44 are attached to the positive mold with a fastener screw 18 through the center hole 74 in the lock mechanism. The center hole 74 is preferably tapped so that various suction adapters and/or cosmetic adapters (not shown) may be threadedly attached thereto. Examples of suitable suction adapters would include a plug to completely seal the center hole, a plug incorporating a one-way valve, and a lock pin cover.

The lock adapter 70 is positioned on the positive mold so that the lock adapter 70 is horizontal to the fill pipe representing the negative cast alignment lines. The lock adapter 70 is positioned on the positive mold so that the knee joint 7 will have the amount of knee rotation as determined by the Prosthetist.

The thermoplastic sheet, cut to the appropriate size, is placed and heated in a wide oven at the appropriate forming temperature. The positive mold is placed horizontally in a vacuum fixture for thermoforming the plastic under negative pressure. The thermoplastic is removed from the oven when the plastic is ready and moldable. The thermoplastic sheet is applied to the positive mold. A seam is formed along the lower aspect of the positive mold. The thermoplastic is pinched along the seam and held until the vacuum pulls in the plastic into all the undercuts so that there are no air voids.

After the thermoplastic cools down the plastic is sanded down on top of the lock mechanism fastener screw 18. The fastener screw 18 is then removed. The fabrication block 38 is trimmed out with a cast cutter and sanding router and the four attachment screws 40 are removed along with the fabrication block 38.

The thermoplastic socket is removed from the positive mold using compressed air, or the mold is broken out of the socket with a pneumatic chisel, or other suitable method is employed.

The thermoplastic socket material is sanded down to the top of the set screws 30 using a sanding router. The set screws 30 are removed with a hex wrench, and the fastener screws 34 with washers 32 are installed and tightened in place of the set screws 30. The edges of the thermoplastic socket material are sanded smooth. The transfemoral prosthesis is assembled with a knee joint 7, pylon 8, ankle assembly 9 and artificial foot 10, as shown in FIG. 1.

Figure 6:
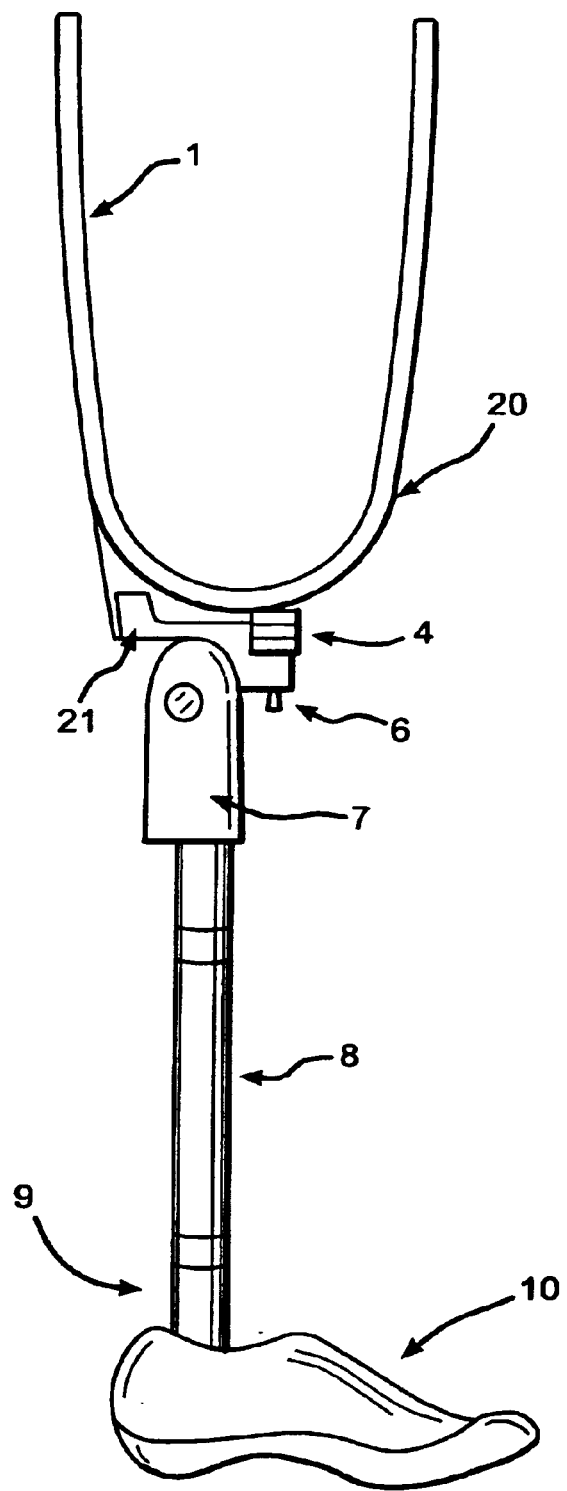
FIG. 6 is a somewhat schematic side elevational view, partially in section, of a finished, thermosetting or laminated type transfemoral socket connected to an artificial leg with a lock adapter in accordance with the invention.

As shown in FIG. 6, the lock adapter 21 of the present invention is used to connect and fabricate a residual limb socket 20 to the lock mechanism 4 and the knee joint 7. In the embodiment of FIG. 6, the prosthesis further includes a pylon 8 which is in turn connected to an artificial foot 10.

Figure 7:
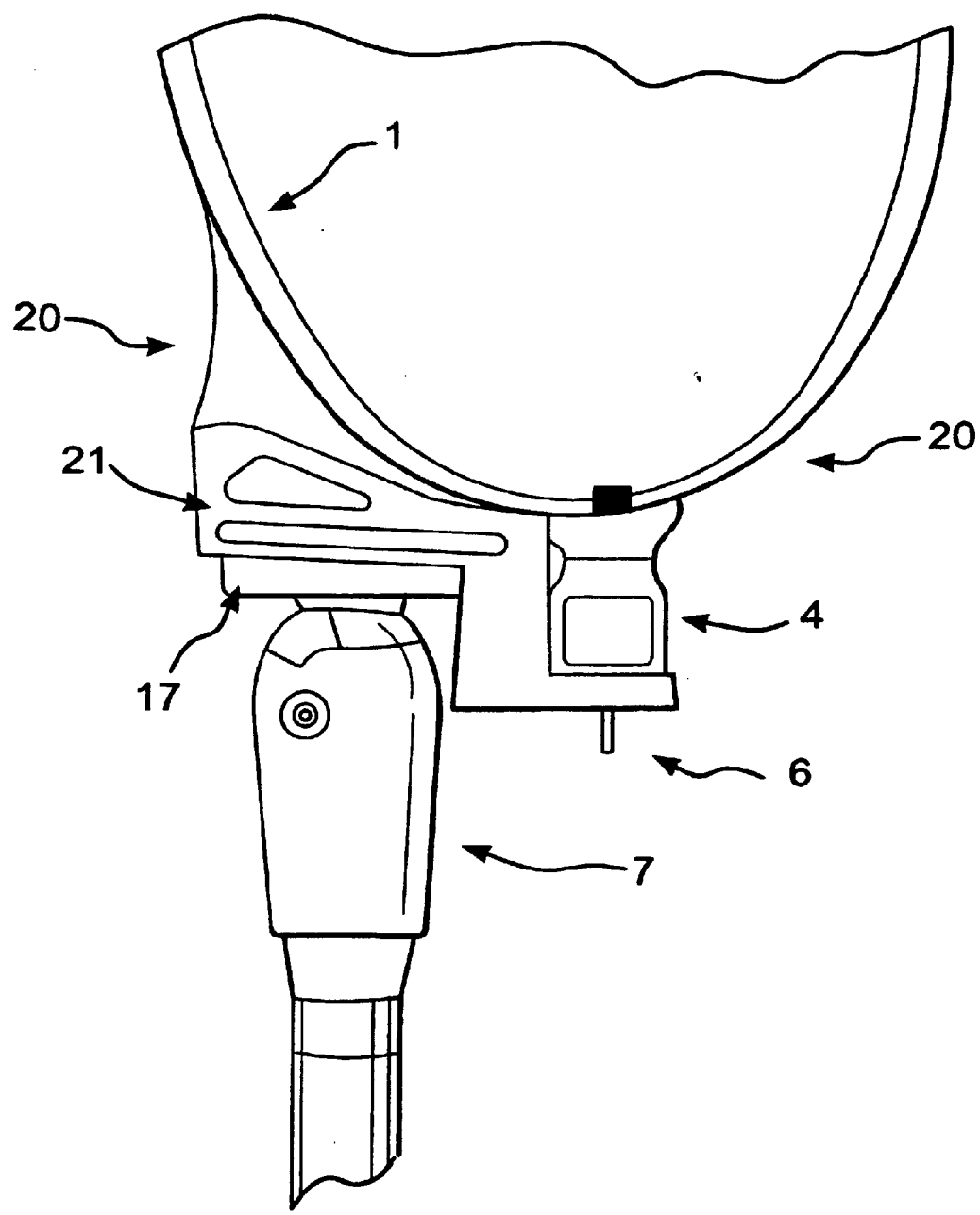
FIG. 7 is an enlarged view, partially in section, of the device shown in FIG. 6.
Figure 8:
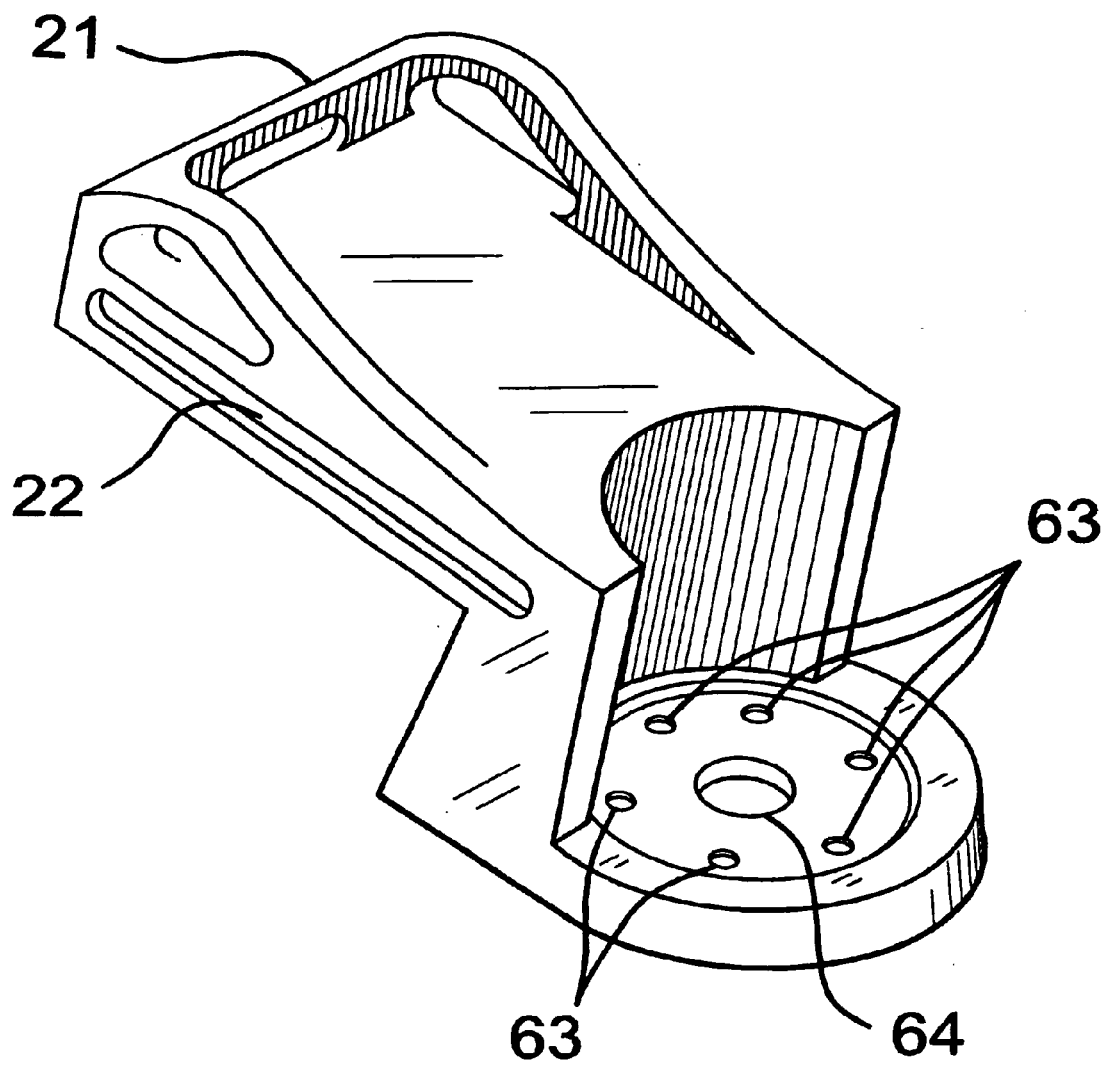
FIG. 8 is a perspective view of the lock adapter shown in FIG. 7.

The generally S-shaped lock adapter 21 of FIG. 7 is used during the fabrication of a laminated or thermosetting resin type socket. As shown in FIG. 8, a perspective view of the lock adapter 21, the lock adapter 21 has through holes 23 used to fasten and reinforce the lock adapter 21 to the transfemoral socket 1 using carbon fiber tape (not shown). The carbon fiber tape is threaded through the holes 23 during the application of the lay-up materials of stockinette for the lamination. The cutout or notched cavities 22 provide additional anchoring to the laminated socket. The drilled through holes 63 are provided to connect the lock mechanism 4 to the lock adapter 21 with fastener screws 36, shown in the exploded perspective view of FIG. 9.

Figure 9:
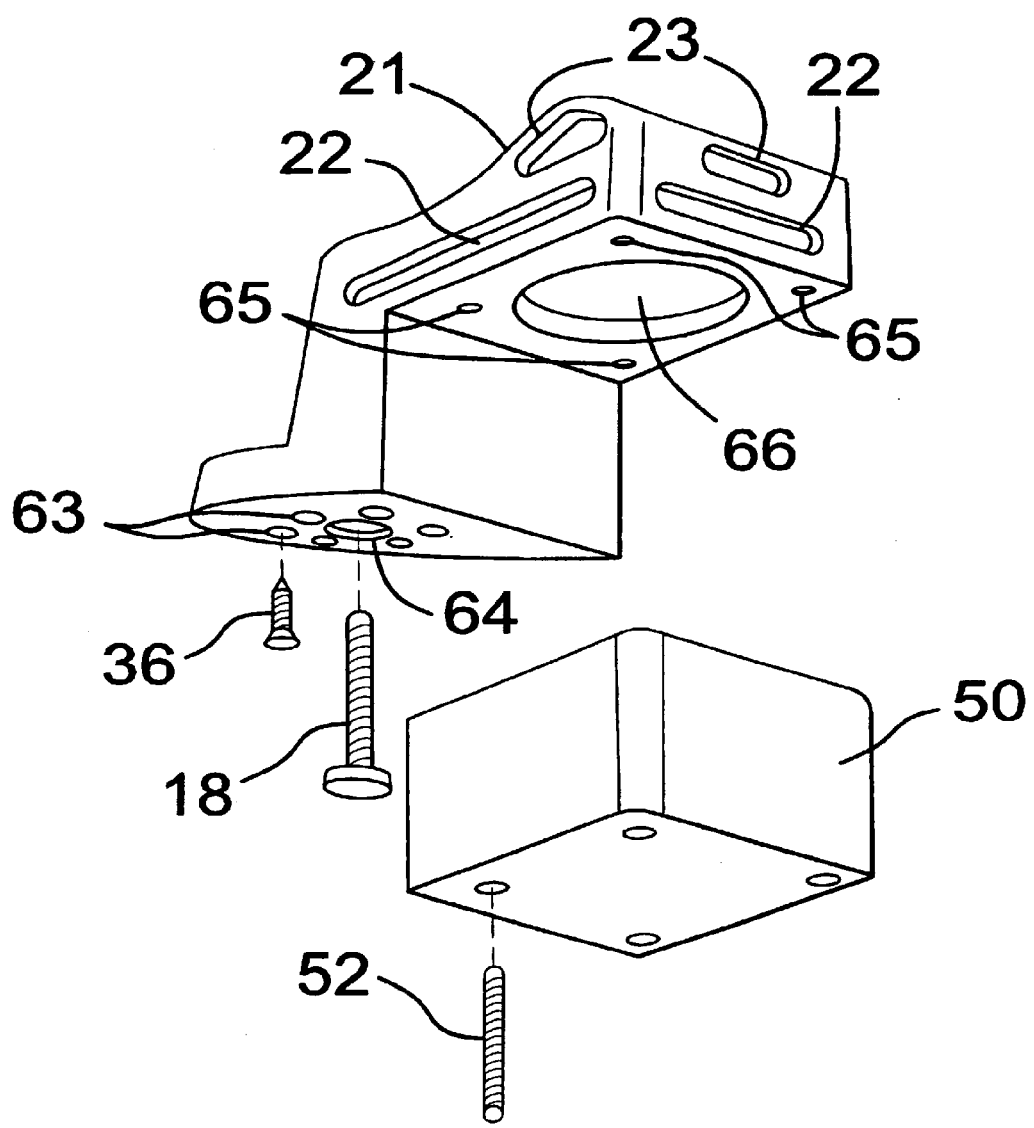
FIG. 9 is an exploded perspective view of the lock adapter shown in FIG. 7 and the fabrication block.

As further shown in FIG. 9, the fabrication block 50 is fastened to the lock adapter 21 via screw holes 65 with the socket head cap screws 52. The knee joint 7 (FIG. 7) is connected to the lock adapter 21 through the four threaded holes 65 with fastener screws either directly, or with a pyramid adapter 17 (FIG. 7).

A preferred method of fabricating the laminated transfemoral socket in accordance with the present invention is as follows. A negative cast is made of the residual limb and suction liner 1 (FIG. 6) with front and side alignment lines. This negative cast is filled with molding plaster and the fill pipe is set parallel to the alignment lines. After the mold has set the negative cast material is removed and the result is a positive cast (not shown).

The positive cast will be used as a model for the transfemoral socket. The positive cast is modified by adding or removing material to achieve proper weight bearing in the transfemoral socket. The modifications are done to the positive cast in accordance with standard principals of prosthetics. The positive cast may also be made by using computer aided design and a computer lathe to manufacture the positive mold.

The positive mold is painted with a mold sealer to reduce moisture. A nylon is applied to the mold to provide a vacuum channel. A polyvinyl acetate (PVA) bag is installed as a separator from the resin.

The locking mechanism 4 shown in FIG. 7 is fastened to the lock adapter 21 with fastener screws 36 (FIG. 9) through the attachment holes 63. The fabrication block 50 is attached to the lock adapter 21 at the four threaded holes 65 with the socket head cap screws 52. The lock adapter 21 and locking mechanism 4 are attached to the positive mold with a fastener screw 18 through the center hole 64 in the lock adapter and lock mechanism. The center hole 64 is preferably tapped so that various suction adapters and/or cosmetic adapters may be threadedly attached thereto. Examples of suitable suction adapters would include a plug to completely seal the center hole, a plug incorporating a one-way valve, and a lock pin cover.

The lock adapter 21 is positioned on the positive mold so that the lock adapter 21 is horizontal to the fill pipe representing the negative cast alignment lines. The lock adapter 21 is positioned on the positive mold so that the knee joint 7 will have the amount of knee rotation as determined by the Prosthetist.

The positive mold is placed in a vacuum fixture for fabrication. A layer of Dacron™ polyester material is applied over the positive mold. The Dacron™ layer is trimmed off around the locking mechanism 4. Several layers of the stockinette are applied to the positive model and trimmed around the lock mechanism. The appropriate amount of stockinette layers are determined by the Prosthetist according to the age, weight and activity level of the amputee.

Carbon tape reinforcement is applied through the through holes 23 of the lock adapter 21. The carbon fiber tape is generally sandwiched midway between the layers of the appropriate layers of stockinette. Several additional layers of stockinette are applied over the complete locking mechanism 4. The layers are twisted and reflected back over the lamination block 50. The appropriate amount of stockinette layers are determined by the Prosthetist according to the age, weight and activity level of the amputee.

The outer PVA bag is applied over the positive model and attached to the vacuum source to provide the negative pressure. The thermosetting resin is poured into the top of the PVA bag and the vacuum source draws resin into the layers of stockinette and carbon. The thermosetting resin is pulled into the stockinette and carbon material by the vacuum or negative pressure during the lamination process. After the thermosetting resin sets and cools, the plastic resin is sanded down on top of the locking mechanism fastener 18, and the fastener screw 18 is removed.

The fabrication block 50 is trimmed out with a cast cutter and sanding router and the four attachment screws 52 are removed along with the fabrication block. The laminated socket is removed from the positive mold using compressed air, or the positive mold is broken out of the socket with a pneumatic chisel, or other suitable method is employed. The edges of the laminated socket material are sanded and buffed smooth. The transfemoral prosthesis is assembled with a knee joint 7, pylon 8, ankle assembly 9 and artificial foot 10, as shown in FIG. 6.

Figure 10:
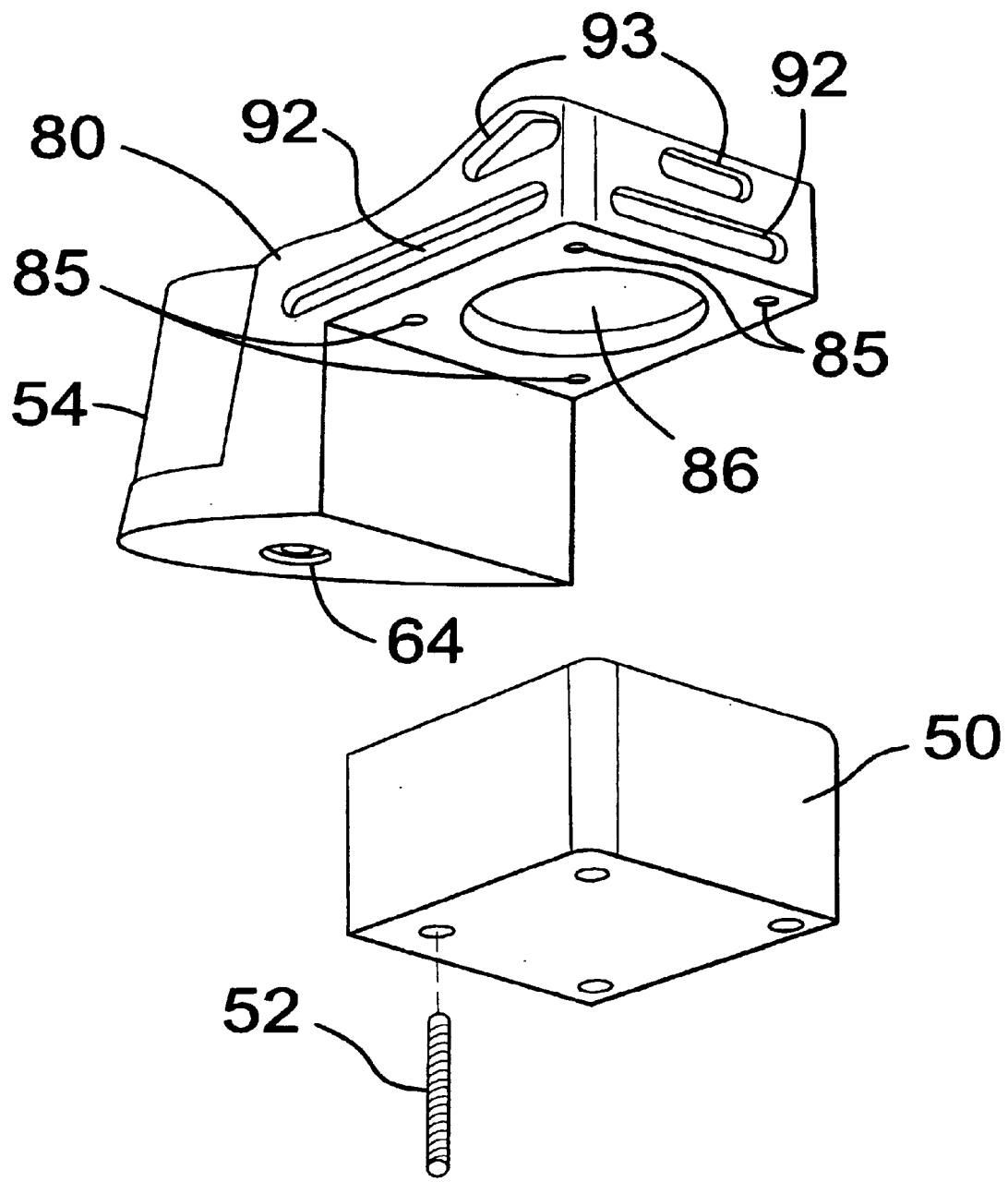
FIG. 10 is an exploded perspective view of another embodiment of the lock adapter with integral locking mechanism for a thermosetting resin or laminated type transfemoral socket.

FIG. 10 shows an exploded perspective view of the lock adapter with integral locking mechanism for a thermosetting resin or laminated type transfemoral socket. In the alternate embodiment shown in FIG. 10, a lock adapter 80 in accordance with the invention has an integral locking mechanism 54 used to connect a residual limb socket 20 (see FIG. 6) to the knee joint 7. The lock adapter 80 is used during the fabrication of a laminated or thermosetting resin type final socket.

As shown in FIG. 10, the lock adapter 80 has through holes 93 used to fasten and reinforce the lock adapter 80 to the transfemoral socket with carbon fiber tape (not shown). The carbon fiber tape is threaded through the holes 93 during the application of the lay-up materials of stockinette for the lamination. The cutout or notched cavities 92 provide additional anchoring to the laminated socket.

As further shown in FIG. 10, the fabrication block 50 is fastened to the lock adapter 80 via screw holes 85 with the socket head cap screws 52. The knee joint 7 is connected to the lock adapter 80 through the four threaded holes 85 with fastener screws, either directly or with a pyramid adapter 17 (FIG. 7).

A preferred method for fabricating the laminated transfemoral socket with lock adapter shown in FIG. 10 is as follows. A negative cast is made of the residual limb and suction liner 1 (FIG. 6) with front and side alignment lines. This negative cast is filled with molding plaster and the fill pipe is set parallel to the alignment lines. After the mold has set the negative cast material is removed and the result is a positive cast.

The positive cast will be used as a model for the transfemoral socket. The positive cast is modified by adding or removing material to achieve proper weight bearing in the transfemoral socket. The modifications are done to the positive cast in accordance with standard principals of prosthetics. The positive cast may also be made by using computer aided design and a computer lathe to manufacture the positive mold.

The positive mold is painted with a mold sealer to reduce moisture. A nylon is applied to the mold to provide a vacuum channel. A PVA bag is installed as a separator from the resin. The fabrication block 50 is attached to the lock adapter 80 at the four threaded holes 85 with the socket head cap screws 52.

The lock adapter 80 and locking mechanism 54 are attached to the positive mold with a fastener screw through the center hole 94 in the locking mechanism 54. The lock adapter 80 is positioned on the positive mold so that the lock adapter 80 is horizontal to the fill pipe representing the negative cast alignment lines. The lock adapter 80 is positioned on the positive mold so that the knee joint 7 will have the amount of knee rotation as determined by the Prosthetist.

The positive mold is placed in a vacuum fixture for fabrication. A layer of Dacron™ material is applied over the positive mold. The Dacron™ material is trimmed off around the lock mechanism. Several layers of the stockinette are applied to the positive model and trimmed around the lock mechanism. The appropriate amount of stockinette layers are determined by the Prosthetist according to the age, weight and activity level of the amputee. Carbon fiber tape reinforcement is applied through the through holes 93 of the lock adapter 80. The carbon fiber tape is generally sandwiched midway between the layers of the appropriate layers of stockinette. Several additional layers of stockinette are applied over the complete locking mechanism. The layers are twisted and reflected back over the lamination block 50. The appropriate amount of stockinette layers are determined by the Prosthetist according to the age, weight and activity level of the amputee.

The outer PVA bag is applied over the positive model and attached to the vacuum source to provide the negative pressure. The thermosetting resin is poured into the top of the PVA bag, and the vacuum source draws resin into the layers of stockinette and carbon fiber. The thermosetting resin is pulled into the stockinette and carbon material by the vacuum or negative pressure during the lamination process. After the thermosetting resin sets and cools, the plastic resin is sanded down on top of the lock mechanism fastener screw 18, and the fastener screw is removed.

The fabrication block 50 is trimmed out with a cast cutter and sanding router and the four attachment screws 52 are removed along with the fabrication block. The laminated socket is removed from the positive mold using compressed air, or the positive mold is broken out of the socket with a pneumatic chisel, or other suitable method is employed. The edges of the laminated socket material are sanded and buffed smooth. The transfemoral prosthesis is assembled with a knee joint 7, pylon 8, ankle assembly 9 and artificial, foot 10, as shown in FIG. 6.

Figure 11:
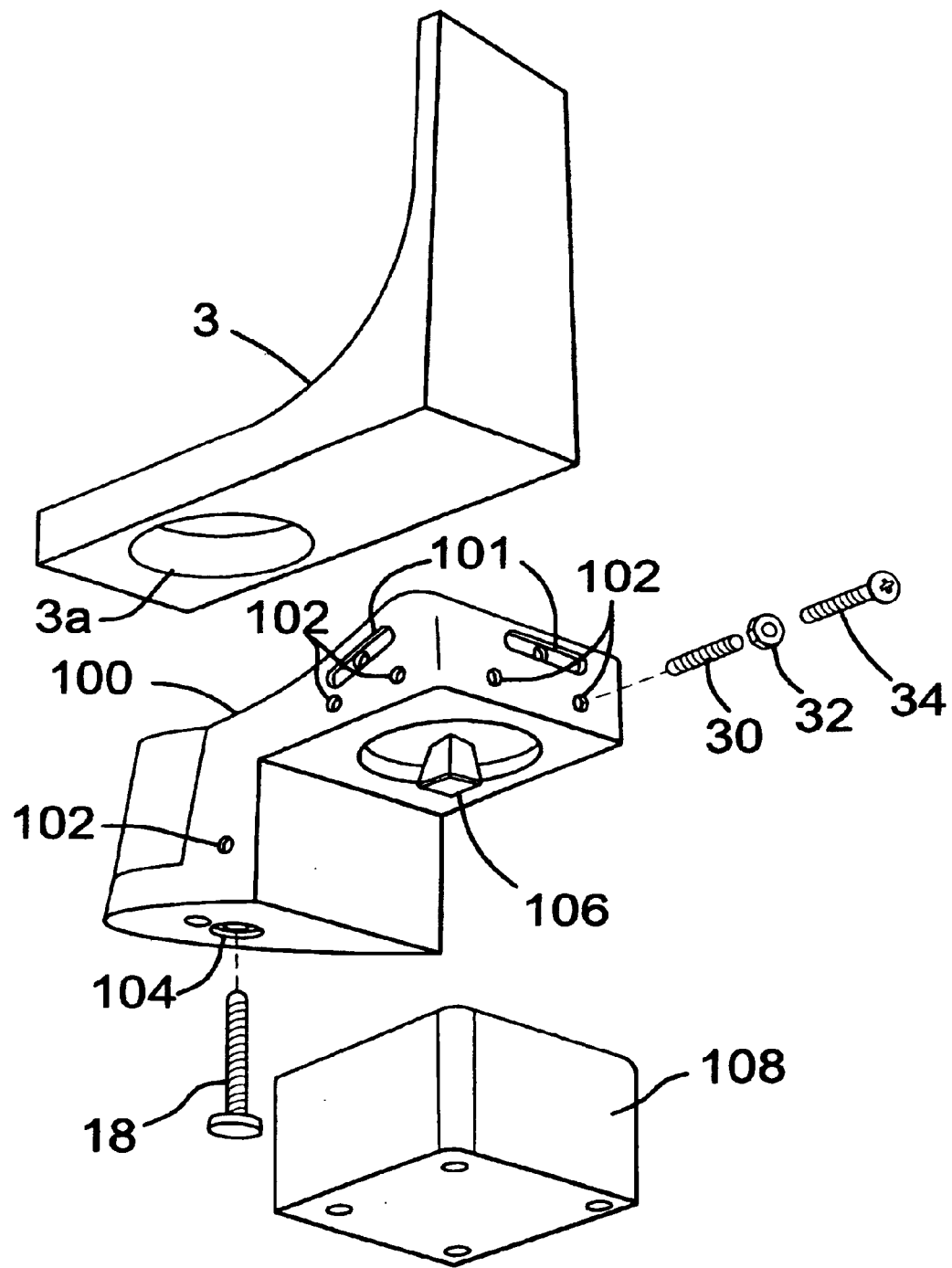
FIG. 11 shows an exploded perspective view of still another embodiment of a lock adapter having an integral locking mechanism and integral pyramid adapter for use in a thermoplastic, transfemoral test socket.

FIG. 11 shows an exploded perspective view of a lock adapter having an integral locking mechanism and integral pyramid adapter for use in a thermoplastic, transfemoral test socket. As illustrated in FIG. 11, the lock adapter 100 with integral locking mechanism 45 is used to connect a residual limb transfemoral socket 2 to the knee joint 7. A generally wedge-shaped posterior foam filler 3 is included to provide the shape of the distal posterior inner aspect of the socket 2. The knee joint 7 is connected to the lock adapter 100 through the pyramid adapter 106, in the same manner as is illustrated in FIG. 2.

As further shown in FIG. 11, the lock adapter 100 has threaded holes 102 which are used to fasten the lock adapter 100 to the transfemoral thermoplastic socket with machine screws 34. The cutout notched cavities 101 provide additional anchoring to the thermoplastic socket.

The posterior foam filler 3 has a cut out hole 3a sized and shaped to fit about the locking mechanism 45. The fabrication block 38 is fastened to the integral pyramid adapter 106 during fabrication of the thermoplastic socket. The set screws 30 are provided to mark the location of the threaded screw holes 102 in the thermoplastic. The set screws 30 are removed after the thermoplastic socket is fabricated. The set screws are replaced with washers 32 and socket head cap screws 34 to fasten the lock adapter to the thermoplastic socket.

A preferred method for fabricating the transfemoral socket of FIG. 11 is as follows. A negative cast is made of the residual limb and suction liner 1 (FIG. 1) with front and side alignment lines. This negative cast is filled with molding plaster and the fill pipe is set parallel to the alignment lines. After the mold has set the negative cast-material is removed and the result is a positive cast.

The positive cast will be used as a model for the transfemoral socket. The positive cast is modified by adding or removing material to achieve proper weight bearing in the transfemoral socket. The modifications are done to the positive cast in accordance with standard principals of prosthetics. The positive cast may also, be made by using computer aided design and a computer lathe to manufacture the positive mold.

The positive mold is painted with a mold sealer to reduce moisture. A nylon is applied to the mold to provide a vacuum channel. The fabrication block 108 is attached to the integral pyramid adapter 106 to facilitate trimming out. The posterior foam filler 3 is placed around the locking mechanism 45 and inside the support walls on the lock adapter 100.

The set screws 30 are installed in the threaded holes 102 to mark the location in the thermoplastic socket. These set screws are left protruding out of the lock adapter an amount sufficient to indicate the location.

The lock adapter 100 and locking mechanism 45 are attached to the positive mold with a fastener screw 18 through the center hole 104 in the lock mechanism. The lock adapter 100 is positioned on the positive mold so that the lock adapter 100 is horizontal to the fill pipe representing the negative cast alignment lines. The lock adapter 100 is positioned on the positive mold so that the knee joint 7 will have the amount of knee rotation as determined by the Prosthetist.

The thermoplastic sheet, cut to the appropriate size, is placed and heated in a wide oven at the appropriate forming temperature. The positive mold is placed horizontally in a vacuum fixture for thermoforming the plastic under negative pressure. The thermoplastic is removed from the oven when the plastic is ready and moldable. The thermoplastic sheet is applied to the positive mold. A seam is formed along the lower aspect of the positive mold. The thermoplastic is pinched along the seam and held until the vacuum pulls in the plastic into all the undercuts so that there are no air voids.

After the thermoplastic cools down, the plastic is sanded down on top of the lock mechanism fastener screw 18. The fastener screw 18 is then removed. The fabrication block 108 is trimmed out with a cast cutter and sanding router and the fabrication block is removed. The thermoplastic socket is removed from the positive mold using compressed air, or the mold is broken out of the socket with a pneumatic chisel, or other suitable method is employed.

The thermoplastic socket material is sanded down to the top of the set screws 30 using a sanding router. The set screws 30 are removed with a hex wrench, and the fastener screws 34 with washers 32 are installed and tightened in place of the set screws 30. The edges of the thermoplastic socket material are sanded smooth. The transfemoral prosthesis is then assembled with a knee joint 7 pylon 8, ankle assembly 9 and artificial foot 10, in the manner shown in FIG. 1.

Figure 12:
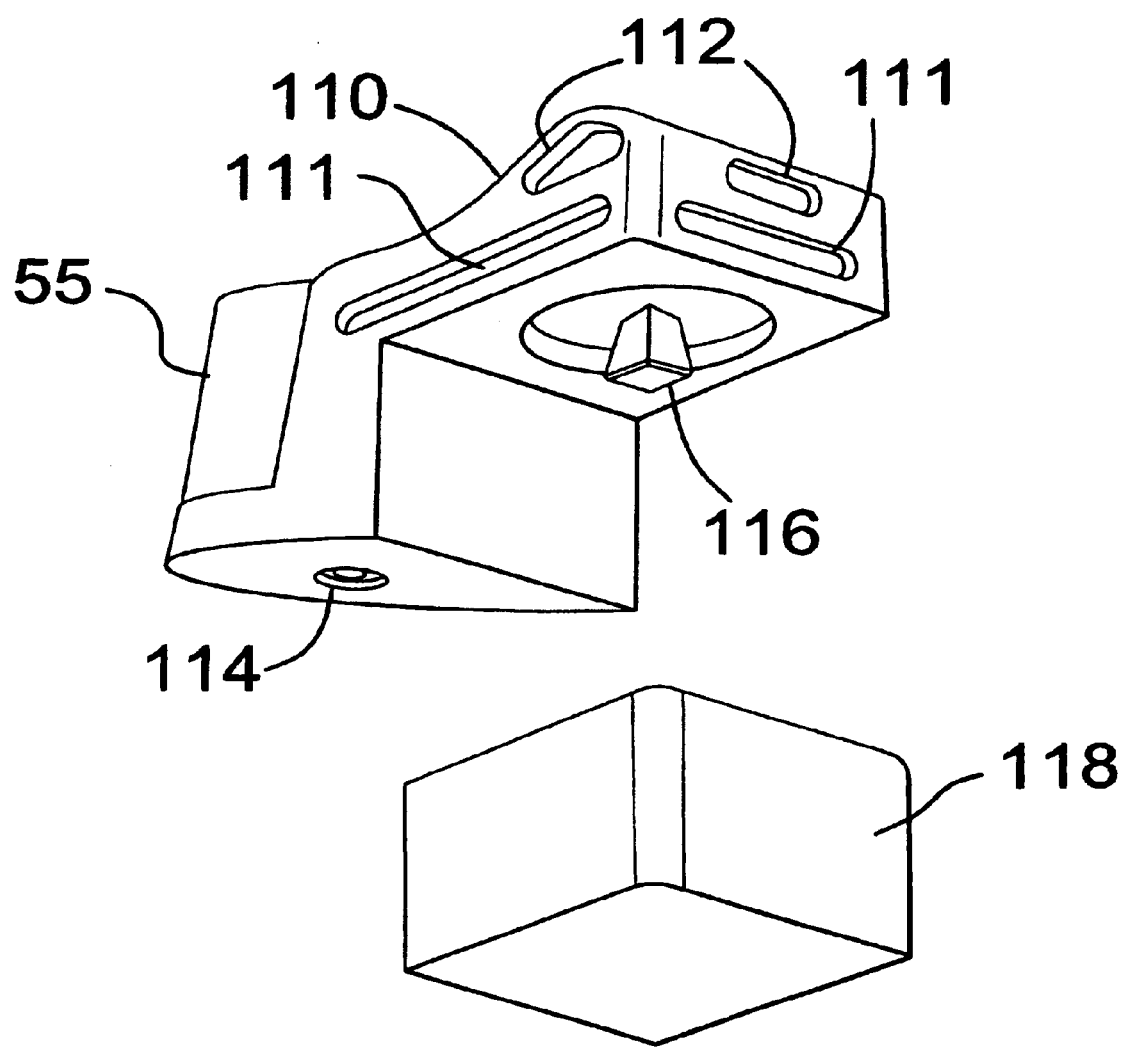
FIG. 12 shows an exploded perspective view of an embodiment of a lock adapter having an integral locking mechanism and integral pyramid adapter for use in a thermosetting resin or laminated type transfemoral socket.

FIG. 12 shows an exploded perspective view of a lock adapter having an integral locking mechanism and integral pyramid adapter for use in a thermosetting resin or laminated type transfemoral socket. As shown in FIG. 12, the lock adapter 110 with integral locking mechanism 55 is used to connect and fabricate a residual limb socket 20 to the knee joint 7 in the manner shown in FIG. 6. In the illustrated embodiment, the prosthesis includes a pylon 8 which is in turn connected to an artificial foot 10. The lock adapter 110 of FIG. 12 is used during the fabrication of a laminated or thermosetting resin type socket.

As further shown in FIG. 12, the lock adapter 110 has through holes 112 used to fasten and reinforce the lock adapter 110 to the transfemoral socket with carbon fiber tape. The carbon fiber tape is threaded through the holes 112 during the application of the lay-up materials of stockinette for the lamination. The cutout or notched cavities 111 provide additional anchoring to the laminated socket.

FIG. 12 also shows the fabrication block 118 fastened to the integral pyramid adapter 116 during the fabrication of the socket. The knee joint 7 is connected to the lock adapter 110 through the integral pyramid adapter 116.

A preferred method for fabricating the laminated transfemoral socket of FIG. 12 is as follows. A negative cast is made of the residual limb and suction liner 1 (FIG. 6) with front and side alignment lines. This negative cast is filled with molding plaster and the fill pipe is set parallel to the alignment lines. After the mold has set the negative cast material is removed and the result is a positive cast.

The positive cast will be used as a model for the transfemoral socket. The positive cast is modified by adding or removing material to achieve proper weight bearing in the transfemoral socket. The modifications are done to the positive cast in accordance with standard principals of prosthetics. The positive cast may also be made by using computer aided design and a computer lathe to manufacture the positive mold.

The positive mold is painted with a mold sealer to reduce moisture. A nylon is applied to the mold to provide a vacuum channel. A PVA bag is installed as a separator from the resin.

The fabrication block 118 of FIG. 12 is attached to the integral pyramid adapter 116 to facilitate trimming out the plastic. The lock adapter 110 and locking mechanism 55 are attached to the positive mold with a fastener screw 18 through the center hole 114 in the locking mechanism.

The lock adapter 110 is positioned on the positive mold so that the lock adapter 110 is horizontal to the fill pipe representing the negative cast alignment lines. The lock adapter 110 is positioned on the positive mold so that the knee joint 7 will have the amount of knee rotation as determined by the Prosthetist.

The positive mold is placed in a vacuum fixture for fabrication. A layer of Dacron™ material is applied over the positive mold. The Dacron™ material is trimmed off around the lock mechanism. Several layers of the stockinette are applied to the positive model and trimmed around the lock mechanism. The appropriate amount of stockinette layers are determined by the Prosthetist according to the age, weight and activity level of the amputee. Carbon fiber tape reinforcement is preferably applied through the through holes 112 of the lock adapter 110. The carbon fiber tape is generally sandwiched midway between the layers of the appropriate layers of stockinette. Several additional layers of stockinette are applied over the complete locking mechanism. The layers are twisted and reflected back over the lamination block 118. The appropriate amount of stockinette layers are determined by the Prosthetist according to the age, weight and activity level of the amputee.

The outer PVA bag is applied over the positive model and attached to the vacuum source to provide the negative pressure; The thermosetting resin is poured into the top of the PVA bag and the vacuum source draws resin into the layers of stockinette and carbon. The thermosetting resin is pulled into the stockinette and carbon material by the vacuum or negative pressure during the lamination process. After the thermosetting resin sets and cools down the plastic resin is sanded down on top of the locking mechanism fastener screw 18, and the fastener screw 18 is removed.

The fabrication block 118 is trimmed out with a cast cutter and sanding router and the fabrication block is removed. The laminated socket is removed from the positive mold using compressed air, or the positive mold is broken out of the socket with a pneumatic chisel, or other suitable method is employed.

The edges of the laminated socket material are sanded and buffed smooth. The transfemoral prosthesis is assembled with a knee joint 7, pylon 8, ankle assembly 9 and artificial foot 10

In accordance with the provisions of the patent statutes, the invention has been described in what is considered to represent its preferred embodiments. However, it should be noted that the invention can be practiced otherwise than as specifically illustrated and described without departing from its spirit or scope.

What is claimed is:

1. A lock adapter for connecting a residual limb liner provided with a locking pin at its lower end to a prosthetic limb, comprising:
   a bracket having a first end and a second end; and
   a lock secured at the first end of the bracket, the lock being adapted to releasably engage the locking pin of the liner;
   the second end of the bracket being adapted to have the prosthetic limb mounted thereto in such a manner that the longitudinal axis of the prosthetic limb is spaced apart from the longitudinal axis of the locking pin of the liner, and wherein the longitudinal axis of the prosthetic limb is positioned at an angle relative to the longitudinal axis of the locking pin of the liner that is greater than 0 degrees.

2. A lock adapter as defined in claim 1, wherein the longitudinal axis of the prosthetic limb is positioned at an angle relative to the longitudinal axis of the locking pin of the liner that is greater than 0 degrees and less than or equal to 25 degrees.

3. A lock adapter as defined in claim 1, wherein the bracket is generally S-shaped, with the first end of the bracket being adapted to be forward of and below the second end of the bracket in use.

4. A lock adapter as defined in claim 1, wherein the lock is formed integrally with the first end of the bracket.

5. A prosthetic device comprising a lock adapter for connecting a residual limb liner provided with a locking pin at its lower end that is releasably engaged with a lock affixed to a prosthetic limb, the lock adapter comprising a bracket having a first end and a second end, the first end of the bracket having a first mounting face against which the lock is secured so as to define a first longitudinal axis perpendicular to the first mounting face, and the second end of the bracket having a second mounting face against which the prosthetic limb is secured so as to define a second longitudinal axis perpendicular to the second mounting face, the bracket being formed so that the first and second longitudinal axes are spaced apart from one another.

6. A lock adapter as defined in 5, wherein the bracket is formed so that the first longitudinal axis is positioned at an angle greater than 0 degrees relative to the second longitudinal axis.

7. A lock adapter as defined in claim 5, wherein the first longitudinal axis is positioned at an angle relative to the second longitudinal axis that is greater than 0 degrees and less than or equal to 25 degrees.

8. A lock adapter as defined in claim 5, wherein the bracket is generally S-shaped, with the first end of the bracket being adapted to be forward of and below the second end of the bracket in use.

9. A lock adapter as defined in claim 5, wherein the lock is formed integrally with the first end of the bracket.

10. A lock adapter as defined in claim 5, wherein the first mounting face is provided with a centrally located, tapped through-hole.

11. A transfemoral prosthetic device comprising:

a residual limb transfemoral socket having a sleeve, an open end adapted to receive a residual limb and a closed end having a through-hole formed therein for receiving a residual limb liner locking pin;

a lock adapter assembly secured to the closed end of the socket, the lock adapter assembly including a generally S-shaped bracket having a first end and a second end and a lock secured at the first end of the bracket, the lock being adapted to releasably engage the locking pin of the liner; and a prosthetic knee joint secured to the second end of the bracket of the lock adapter assembly.

12. A lock adapter for connecting a residual limb liner provided with a locking pin at its lower end to a prosthetic limb, comprising:

a bracket having a first end and a second end; and a lock secured at the first end of the bracket, the lock being adapted to releasably engage the locking pin of the liner;

the second end of the bracket being adapted to have the prosthetic limb mounted thereto in such a manner that the longitudinal axis of the prosthetic limb is spaced apart from the longitudinal axis of the locking pin of the liner, and wherein the bracket is generally S-shaped, with the first end of the bracket being adapted to be forward of and below the second end of the bracket in use.

* * * * *